(12) United States Patent
Hitchcock et al.

(10) Patent No.: US 11,435,274 B2
(45) Date of Patent: Sep. 6, 2022

(54) CONTINUOUS MUD RHEOLOGY MONITORING

(71) Applicant: Saudi Arabian Oil Company, Dhahran (SA)

(72) Inventors: Graham Hitchcock, Aberdeenshire (GB); Michael Affleck, Aberdeenshire (GB)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 289 days.

(21) Appl. No.: 16/893,286

(22) Filed: Jun. 4, 2020

(65) Prior Publication Data

US 2021/0381942 A1 Dec. 9, 2021

(51) Int. Cl.
*G01N 11/04* (2006.01)
*E21B 21/08* (2006.01)
*G01N 33/28* (2006.01)
*E21B 21/06* (2006.01)

(52) U.S. Cl.
CPC .............. *G01N 11/04* (2013.01); *E21B 21/08* (2013.01); *G01N 33/2823* (2013.01); *E21B 21/065* (2013.01)

(58) Field of Classification Search
CPC .... G01N 11/04; G01N 33/2823; E21B 21/01; E21B 21/08
See application file for complete search history.

(56) References Cited

U.S. PATENT DOCUMENTS

| 2,489,180 | A | * | 11/1949 | Hayward | E21B 49/005 73/152.04 |
| 3,468,158 | A | * | 9/1969 | Chien | G01N 11/08 73/54.05 |
| 3,885,429 | A | | 5/1975 | Megyeri et al. | |

(Continued)

FOREIGN PATENT DOCUMENTS

EP 0458391 A1 11/1991
WO 2013112274 A1 8/2013

OTHER PUBLICATIONS

International Search Report and Written Opinion for PCT Application No. PCT/US2021/0035637 dated Sep. 9, 2021.

(Continued)

*Primary Examiner* — John Fitzgerald
(74) *Attorney, Agent, or Firm* — Bracewell LLP; Constance G. Rhebergen; Linda L. Morgan

(57) ABSTRACT

Systems and methods for determining rheology characteristics of a drilling fluid include a drop-in unit sized to fit within a flowline of a drilling fluid circulation system upstream of a mud shaker. The drop-in unit has an entry funnel having an end plate with an opening through the end plate. The entrance of the entry funnel has an outer diameter that is larger than a diameter of the opening through the end plate. An instrumentation tubular is an elongated member with an inner bore that is in fluid communication with the opening through the end plate. The instrumentation tubular includes a downstream sensor and an upstream sensor. The upstream and downstream sensors are operable to sense a parameter of the drilling fluid traveling through the instrumentation tubular for calculating a change of viscosity of the drilling fluid within the flowline between a first time and a second time.

22 Claims, 4 Drawing Sheets

(56) References Cited

U.S. PATENT DOCUMENTS

| | | | |
|---|---|---|---|
| 4,726,219 A | 2/1988 | Pearson et al. | |
| 4,821,564 A * | 4/1989 | Pearson | G01N 11/08 |
| | | | 73/152.52 |
| 4,876,902 A * | 10/1989 | von Alfthan | G01N 1/2035 |
| | | | 73/863.83 |
| 5,063,776 A | 11/1991 | Zanjer et al. | |
| 6,805,674 B2 * | 10/2004 | Kensey | A61B 5/150221 |
| | | | 600/573 |
| 8,056,400 B2 * | 11/2011 | Reintjes | G01N 1/2035 |
| | | | 73/863.23 |
| 8,151,633 B2 | 4/2012 | Jamison et al. | |
| 8,392,121 B2 | 3/2013 | Zamora et al. | |
| 8,997,562 B2 * | 4/2015 | Schexnaider | E21B 49/005 |
| | | | 73/152.19 |
| 9,638,618 B2 | 5/2017 | Mllard et al. | |
| 10,227,838 B2 | 3/2019 | Dillard et al. | |
| 10,385,636 B2 | 8/2019 | Midlang et al. | |
| 10,415,352 B2 * | 9/2019 | Thomas | E21B 43/086 |
| 10,564,083 B2 * | 2/2020 | Spoerker | E21B 21/01 |
| 10,859,481 B2 * | 12/2020 | van Oort | E21B 21/01 |
| 2009/0216465 A1 * | 8/2009 | Millet | B01L 3/0217 |
| | | | 702/50 |
| 2011/0185795 A1 | 8/2011 | Colquhoun | |
| 2013/0319104 A1 * | 12/2013 | Schexnaider | G01N 1/2294 |
| | | | 73/152.42 |
| 2014/0144225 A1 | 5/2014 | Johnson et al. | |
| 2014/0262516 A1 | 9/2014 | Larson | |
| 2015/0330213 A1 | 11/2015 | Van Oort et al. | |
| 2017/0097293 A1 | 4/2017 | Tozzi et al. | |
| 2017/0276584 A1 | 9/2017 | Ye | |
| 2017/0336310 A1 | 11/2017 | Spoerker | |
| 2018/0313178 A1 * | 11/2018 | Biggerstaff | E21B 21/08 |
| 2019/0094119 A1 | 3/2019 | Singh et al. | |
| 2019/0178770 A1 | 6/2019 | Marum et al. | |
| 2019/0309589 A1 | 10/2019 | Torjussen et al. | |
| 2019/0309614 A1 | 10/2019 | Benson | |
| 2020/0340791 A1 * | 10/2020 | Bouldin | E21B 7/26 |
| 2020/0399967 A1 * | 12/2020 | Biggerstaff | E21B 21/065 |
| 2021/0002970 A1 * | 1/2021 | Nesheim | E21B 49/08 |
| 2021/0381942 A1 * | 12/2021 | Hitchcock | E21B 21/01 |
| 2022/0003649 A1 * | 1/2022 | Khorshidian | G01N 11/08 |

OTHER PUBLICATIONS

Alakbari et al., "Prediction of Bubble Point Pressure Using Artificial Intelligence AI Techniques", Society of Petroleum Engineers, 184208-MS, 2016.

Marshall, C., "Advances in Flow Measurement Using a Frictional Pressure Drop", North Sea Flow Measurement Workshop, Oct. 22-24, 2018.

Elyas et al., "Using Real Time FLuid Properties Data in Providing Accurate Results for Managed Pressure Drilling and Improved Drilling Control", SPEI/IADC Managed Pressure Drilling & Underbalanced Operations Conference & Exhibition, 190007-MS, 2018.

Vajargah et al., "Automated Drilling Fluid Rheology Characterization with Downhole Pressure Sensor Data", SPE/IADC Drilling Conference and Exhibition, 173085-MS, 2015.

* cited by examiner

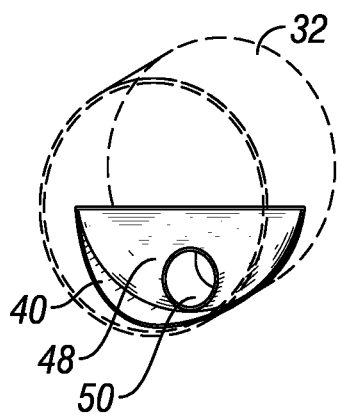
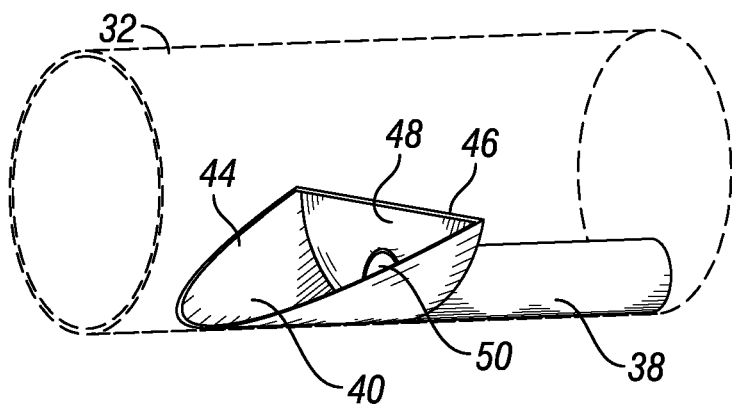
FIG. 4  FIG. 5
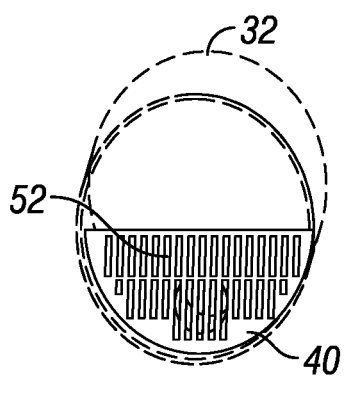
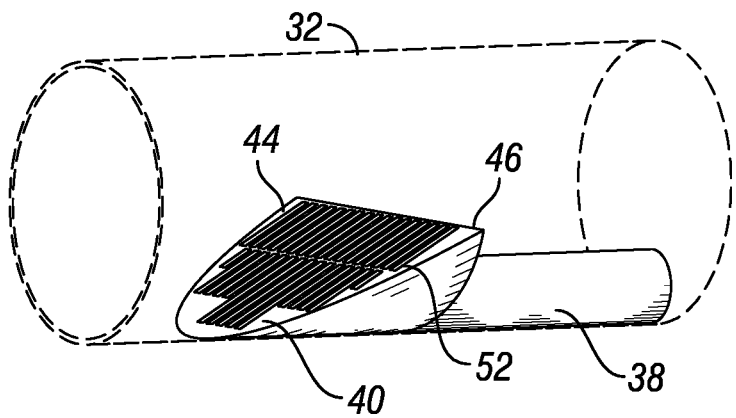
FIG. 6  FIG. 7

CONTINUOUS MUD RHEOLOGY MONITORING

BACKGROUND OF THE DISCLOSURE

1. Field of the Disclosure

The present disclosure relates to subterranean well development, and more specifically, the disclosure relates to the measurement of drilling fluid properties.

2. Description of the Related Art

Drilling fluid measurement is an essential part of subterranean well drilling operations. Measurements of the properties of drilling fluid are critical for maintaining well control. In currently available measurement systems, samples of drilling fluid can be taken from the mud tanks periodically, such as every six to eight hours. These samples can be analyzed under laboratory conditions using rheometers to give a report of absolute rheological data. The resulting drilling fluid data can be used in drilling simulation programs.

There are also currently available 'on line' drilling fluid analysis equipment. This type of equipment can be a set of laboratory type measuring equipment that is fed through a bleed off line from a well return line. This type of equipment typically requires constant attention and a high level of maintenance.

SUMMARY OF THE DISCLOSURE

Embodiments of the current application provide systems and method a modular self-contained drilling fluid rheology measurement device in the form of a drop-in unit. The drop-in unit is installed into the mud return line upstream of the mud conditioning units or mud shakers, therefore monitoring the drilling fluid as it exits the well annulus. The drop-in unit can provide constant real time mud rheology data. A fluid viscosity calculation can be performed using frictional pressure drop and flow rate over a length of the drop-in unit.

Systems and methods of this disclosure can utilize the viscosity readings to provide a constant real-time indication of viscosity change during the drilling operations. The resulting trend analysis can highlight changes in drilling fluid viscosity. In certain embodiments, the viscosity readings can further be combined with standard lab results taken at various flow rates using a predictive trend analysis software package. Predictive algorithms can use the detailed measurements from the lab results that are taken using standard API recommended equipment and conditions at given time intervals, together with the trend analysis obtained from the drop-in unit to predict drilling fluid properties in real time from the mud return line.

In an embodiment of this disclosure, a system for determining rheology characteristics of a drilling fluid include a drop-in unit sized to fit within a flowline of a drilling fluid circulation system upstream of a mud shaker. The drop-in unit has an entry funnel, the entry funnel having an entrance end oriented with an entrance facing in an upstream direction within the flowline, and a tube end opposite the entrance end, the tube end having an end plate with an opening through the end plate, the entrance end having an outer diameter that is larger than a diameter of the opening through the end plate. The drop-in unite further includes an instrumentation tubular. The instrumentation tubular is an elongated member with an inner bore that is in fluid communication with the opening through the end plate. The instrumentation tubular includes a downstream sensor and an upstream sensor. The upstream sensor and the downstream sensor are operable to sense a parameter of the drilling fluid traveling through the inner bore of the instrumentation tubular for calculating a change of viscosity of the drilling fluid within the flowline between a first time and a second time.

In alternate embodiments of this disclosure, an anchor section can be at a downstream end of the drop-in unit, and be operable to anchor the drop-in unit within the flowline. A flange connector can be located at a downstream end of the drop-in unit, and be operable to connect the drop-in unit to a flange of the flowline. The drop-in unit can be formed of a plurality of unit sections. Each of the unit sections can be secured to an adjacent unit section with a quick-connect connector. An alignment apparatus can be operable to circumferentially orient each of the unit sections to the adjacent unit section. Each of the unit sections can have a length in a range of 1 meter to 1.5 meters and can have a diameter in a range of 76 millimeters to 152 millimeters.

In other alternate embodiments, the end plate can have a vertical height such that the end plate acts as a weir, increasing a height of a level of fluid upstream of the end plate compared to a height of a level of fluid downstream of the end plate. A debris protector can extend across the entrance end of the entry funnel. The debris protector can have openings sized to allow a passage of fluid through the debris protector and to prohibit a passage of certain debris through the debris protector. The downstream sensor can include a downstream pressure sensor and the upstream sensor can include an upstream pressure sensor.

In still other embodiments, the downstream sensor can further include a downstream temperature sensor and the upstream sensor further includes an upstream temperature sensor. The downstream temperature sensor and the upstream temperature sensor can be operable to sense a temperature of the drilling fluid traveling through the inner bore of the instrumentation tubular, for calculating a temperature corrected change of viscosity of the drilling fluid within the flowline between the first time and the second time. The inner bore of the instrumentation tubular can include a change in diameter between the downstream sensor and the upstream sensor.

In another embodiment of this disclosure, a method for determining rheology characteristics of a drilling fluid include installing a drop-in unit within a flowline of a drilling fluid circulation system upstream of a mud shaker. The drop-in unit has an entry funnel. The entry funnel has an entrance end oriented with an entrance facing in an upstream direction within the flowline, and a tube end opposite the entrance end. The tube end has an end plate with an opening through the end plate. The entrance end has an outer diameter that is larger than a diameter of the opening through the end plate. The drop-in unit further includes an instrumentation tubular. The instrumentation tubular is an elongated member with an inner bore that is in fluid communication with the opening through the end plate. The instrumentation tubular includes a downstream sensor and an upstream sensor. At a first time, a first downstream fluid parameter of the drilling fluid traveling through the inner bore of the instrumentation tubular is sensed at the downstream sensor, and a first upstream parameter of the drilling fluid traveling through the inner bore of the instrumentation tubular is sensed at the upstream sensor. A first fluid viscosity is calculated. At a second time, a second downstream fluid parameter of the drilling fluid traveling through the inner bore of the instrumentation tubular is sensed at the downstream sensor, and a second upstream parameter of the drilling fluid traveling through the inner bore of the instrumentation tubular is sensed at the upstream sensor. A second fluid viscosity is calculated. The second fluid viscosity is compared to the first fluid viscosity to determine a change of viscosity of the drilling fluid within the flowline between the first time and the second time.

In alternate embodiments, the method can further include anchoring a downstream end of the drop-in unit within the flowline. A downstream end of the drop-in unit can be secured to a flange of the flowline. The drop-in unit can be formed from a plurality of unit sections, each of the unit sections secured to an adjacent unit section with a quick-connect connector. Each of the unit sections can be circumferentially oriented to the adjacent unit section with an alignment apparatus. Each of the unit sections can have a length in a range of 1 meter to 1.5 meters and can have a diameter in a range of 76 millimeters to 152 millimeters.

In other alternate embodiments, the method can further include increasing a height of a level of fluid upstream of the end plate compared to a height of a level of fluid downstream of the end plate by providing the end plate with a vertical height such that the end plate acts as a weir. A debris protector can extend across the entrance end of the entry funnel, the debris protector having openings sized to allow a passage of fluid through the debris protector and to prohibit a passage of certain debris through the debris protector. The inner bore of the instrumentation tubular can include a change in diameter between the downstream sensor and the upstream sensor.

In still other alternate embodiments, the downstream sensor can include a downstream pressure sensor and the upstream sensor can include an upstream pressure sensor. The downstream sensor can alternately further include a downstream temperature sensor and the upstream sensor can alternately further includes an upstream temperature sensor. The method can further include at the first time, measuring a first downstream temperature and a first upstream temperature of the drilling fluid traveling through the inner bore of the instrumentation tubular. A temperature corrected first fluid viscosity can be calculated. At the second time, a second downstream temperature and a second upstream temperature of the drilling fluid traveling through the inner bore of the instrumentation tubular can be measured. A temperature corrected second fluid viscosity can be calculated. A temperature corrected change of viscosity of the drilling fluid within the flowline between the first time and the second time can be determined.

BRIEF DESCRIPTION OF THE DRAWINGS

So that the manner in which the features, aspects and advantages of the embodiments of this disclosure, as well as others that will become apparent, are attained and can be understood in detail, a more particular description of the disclosure may be had by reference to the embodiments thereof that are illustrated in the drawings that form a part of this specification. It is to be noted, however, that the appended drawings illustrate only certain embodiments of the disclosure and are, therefore, not to be considered limiting of the disclosure's scope, for the disclosure may admit to other equally effective embodiments.

FIG. 4 is a perspective view of an entry funnel of a drop-in unit of a system for determining rheology characteristics of a drilling fluid, in accordance with an embodiment of this disclosure.

FIG. 5 is another perspective view of the entry funnel of FIG. 4.

FIG. 6 is a perspective view of an entry funnel of a drop-in unit of a system for determining rheology characteristics of a drilling fluid, in accordance with an embodiment of this disclosure, shown with a debris protector.

FIG. 7 is another perspective view of the entry funnel of FIG. 6.

DETAILED DESCRIPTION

The disclosure refers to particular features, including process or method steps. Those of skill in the art understand that the disclosure is not limited to or by the description of embodiments given in the specification. The subject matter of this disclosure is not restricted except only in the spirit of the specification and appended Claims.

Those of skill in the art also understand that the terminology used for describing particular embodiments does not limit the scope or breadth of the embodiments of the disclosure. In interpreting the specification and appended Claims, all terms should be interpreted in the broadest possible manner consistent with the context of each term. All technical and scientific terms used in the specification and appended Claims have the same meaning as commonly understood by one of ordinary skill in the art to which this disclosure belongs unless defined otherwise.

As used in the Specification and appended Claims, the singular forms "a", "an", and "the" include plural references unless the context clearly indicates otherwise.

As used, the words "comprise," "has," "includes", and all other grammatical variations are each intended to have an open, non-limiting meaning that does not exclude additional elements, components or steps. Embodiments of the present disclosure may suitably "comprise", "consist" or "consist essentially of" the limiting features disclosed, and may be practiced in the absence of a limiting feature not disclosed. For example, it can be recognized by those skilled in the art that certain steps can be combined into a single step.

Where a range of values is provided in the Specification or in the appended Claims, it is understood that the interval encompasses each intervening value between the upper limit and the lower limit as well as the upper limit and the lower limit. The disclosure encompasses and bounds smaller ranges of the interval subject to any specific exclusion provided.

As used in this Specification, the term "substantially equal" means that the values being referenced have a difference of no more than two percent of the larger of the values being referenced.

Where reference is made in the specification and appended Claims to a method comprising two or more defined steps, the defined steps can be carried out in any order or simultaneously except where the context excludes that possibility.

Figure 1:
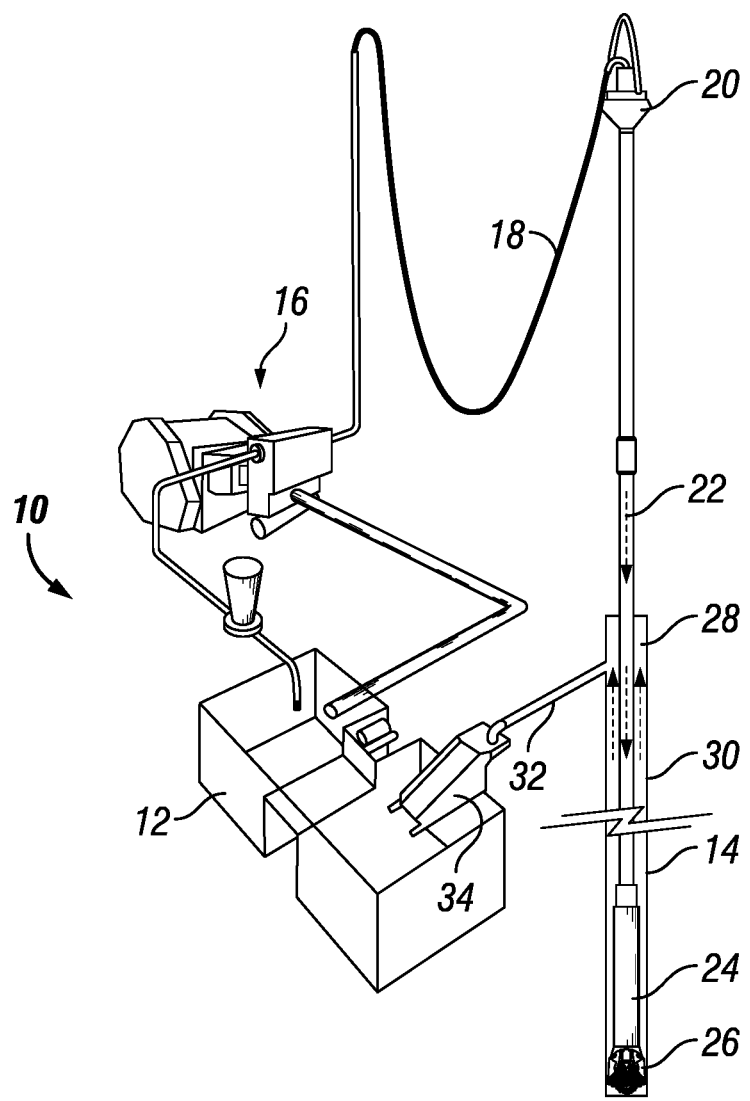
FIG. 1 is a schematic perspective view of a drilling fluid circulation system with a system for determining rheology characteristics of a drilling fluid, in accordance with an embodiment of this disclosure.

Looking at FIG. 1, drilling fluid circulation system 10 includes mud tank 12. Mud tank 12 are located at an earth's surface and are used to store drilling fluid that is to be delivered to subterranean well 14. Pump system 16 is used to pump the drilling fluid from mud tank 12 into hose 18. Hose 18 extends to swivel assembly 20 that is located axially above subterranean well 4. The drilling fluid can be delivered into the bore of drilling tubular 22, travel in a downhole direction through the bore of drilling tubular 22, and out of bottom hole assembly 24 or drill bit 26. The drilling fluid can then travel in an uphole direction through annulus 28. Annulus 28 is defined between an outer diameter surface of drilling tubular 22 and an inner diameter surface of wellbore 30. Wellbore 30 is the drilled with drill bit 26.

After exiting annulus 28, the drilling fluid enters a flow line, such as mud line 32. Mud line 32 extends from annulus 28 to mud shaker 34. Mud line 32 can be either an open channel or a closed pipe. Mud shaker 34 can separate solid material that is within the drilling fluid before the drilling fluid is delivered back into the mud tank 12. A system for determining rheology characteristics of the drilling fluid can be located in mud line 32, downstream of annulus 28 and upstream of mud shaker 34.

Figure 2:
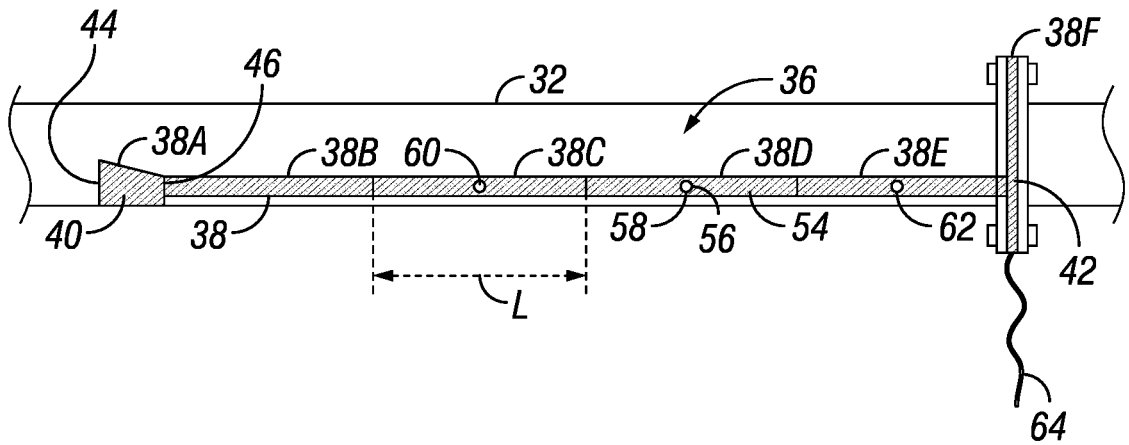
FIG. 2 is a section view of a drop-in unit of a system for determining rheology characteristics of a drilling fluid, in accordance with an embodiment of this disclosure.
Figure 3:
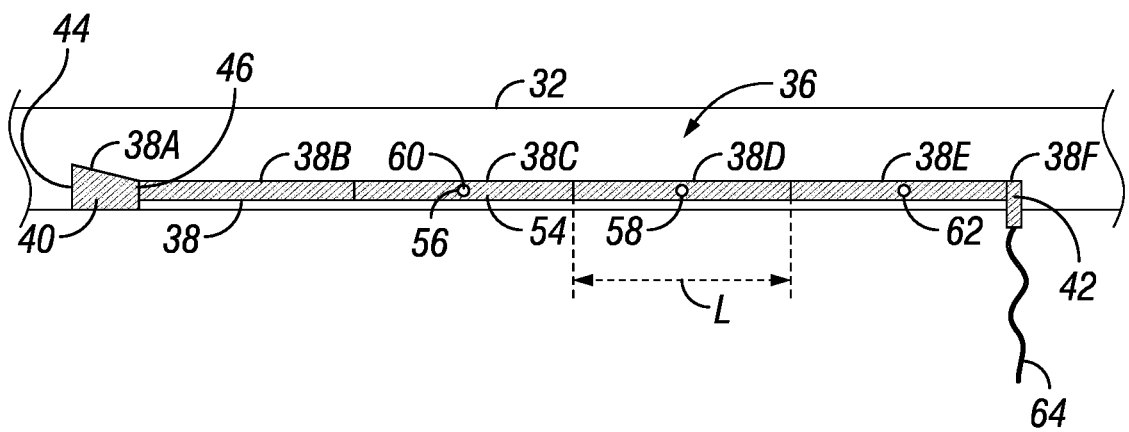
FIG. 3 is a section view of a drop-in unit of a system for determining rheology characteristics of a drilling fluid, in accordance with an embodiment of this disclosure.

Looking at FIGS. 2-3, the system for determining rheology characteristics of the drilling fluid includes drop-in unit 36. Drop-in unit 36 has a modular design that allows drop-in unit 36 to be assembled and configured at the well site. After being installed in mud line 32, drop-in unit 36 is a completely standalone unit.

Drop-in unit 36 can be used as a viscometer, and not as a rheometer, to track changes in viscosity in real time. A rheometer is an instrument used to measure the viscosity of a fluid where the viscosity will vary with flow conditions. A rheometer measures the way in which a d flows in response to applied forces. A rheometer is used to measure properties of fluids which cannot be defined by a single value of viscosity and instead require a variety of parameters to be set and measured. Embodiments of this disclosure include a viscometer that is not a rheometer.

A viscometer measures a viscosity of a fluid under a single flow condition. In general, a viscometer used in embodiments of this disclosure is stationary and drag caused by relative motion of the drilling fluid flowing past a stationary surface is measured to determine the viscosity of the drilling fluid. In embodiments of this disclosure, there is no flow rate control mechanism that is part of drop-in unit 36. The viscosity measurements are obtained by data sensed by drop-in unit 36 at the flow rate that results from drilling fluid flow at operational flow rates. In certain embodiments, the flow rate can be measured by drop-in unit 36, but is not controllable by drop-in unit 36.

As described in further detail, drop-in unit 36 can measure a pressure differential between two points along the length of drop-in unit 36. A temperature can also be measured at the two points so that the viscosity calculation can be temperature corrected. In certain embodiments, the flow rate can further be measured at the two points.

Drop-in unit 36 can be made up of unit sections 38 that are axially aligned and connected together. The number and type of unit sections 38 that are used to make up drop-in unit 36 will be dependent on the design of mud line 32 and the operational requirements of drop-in unit 36, such as the number of sensors required in drop-in unit 36. In the example embodiments of FIGS. 2-3, drop-in unit 36 is formed of six unit sections 38, which are labeled 38A-38F. In embodiments of this application, each unit section 38 can have a length L in a range of 1 meter to 1.5 meters and can have a diameter in a range of 76 millimeters to 152 millimeters.

Unit sections 38 of drop-in unit 36 can be formed of a material that is cost effective and light in weight for ease of transportation to the drilling site. As an example, unit sections 38 of drop-in unit 36 can be formed of a composite material, such as a glass reinforced plastic, or a metal material, such as aluminum or steel. The material used to form unit sections 38 of drop-in unit 36 will be resistant to drilling fluids at ambient and raised operational temperatures. That is, the material used to form unit sections 38 will be selected to reduce the risk of damage or failure of the material due to corrosive chemicals, pressures, and temperatures to which drop-in unit 36 will be exposed within mud line 32.

In the example embodiment of FIGS. 2-3, three different types of unit sections 38 are shown. The upstream-most unit section 38A is entry funnel 40. The downstream-most unit section 38F is an anchor section 42. The unit sections 38 located between entry funnel 40 and anchor section 42 can include pipe sections without any instrumentation, or pipe sections that have instrumentation.

Entry funnel 40 has an entrance end 44 that is oriented with an opening facing in an upstream direction within mud line 32. Entry funnel 40 has tube end 46 opposite entrance end 44. Looking at FIGS. 4-7, in an example embodiment, tube end 46 can include end plate 48. Opening 50 extends through end plate 48. Opening 50 is in fluid communication with the tubular member of the adjacent unit section 38. End plate 48 can be secured to the adjacent unit section 38.

Entry funnel 40 can be funnel or scoop shaped. The entrance end 44 of entry funnel 40 has an outer diameter that is larger than the diameter of opening 50 through end plate 48. Entry funnel can have an outer diameter shape and size that corresponds to the bore of mud line 32. Therefore, entry funnel 40 will be particular to a size of mud line 32, whereas pipe sections of drop-in unit 36 are generic and can be used in any mud line 32. Entry funnel 40 directs drilling fluid flowing through mud line 32 towards opening 50 so that drop-in unit 36 can remain completely full of drilling fluid.

Figure 8:
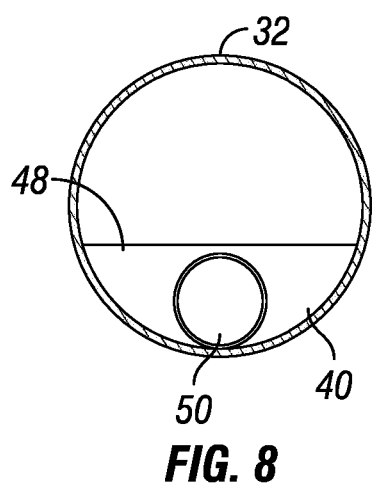
FIG. 8 is an end view of an end plate the drop-in unit of the system for determining rheology characteristics of a drilling fluid, in accordance with an embodiment of this disclosure.
Figure 9:
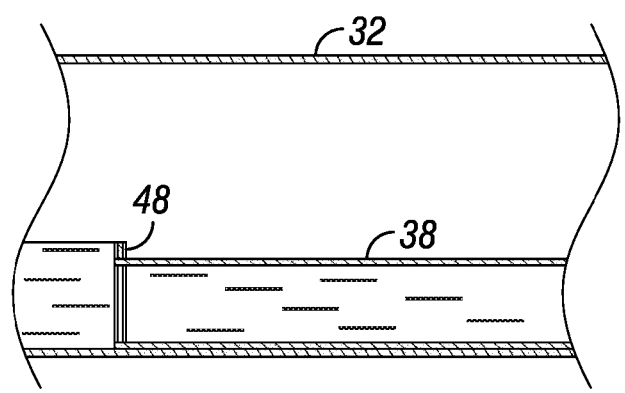
FIG. 9 is a section view of the drop-in unit of FIG. 8.

In order to further assure that the unit sections 38 of drop-in unit 36 can remain completely full of drilling fluid, even if mud line 32 itself is not full, end plate 48 can act as a weir. Looking at FIGS. 8-9, end plate 48 can have a vertical height that is larger than the height of the tubular of adjacent unit section 38. The height of end plate 48 will block the flow of drilling fluid, increasing the height of a level of the drilling fluid upstream of end plate 48 compared to a height of a level of the drilling fluid downstream of end plate 48.

Looking at FIGS. 6-7, entry funnel 40 can optionally include debris protector 52. Debris protector 52 can extend across entrance end 44. Debris protector 52 can have openings sized to allow for the passage of drilling fluid through debris protector 52, and to prohibit the passage of certain debris through debris protector 52. As an example large debris traveling through drop-in unit 36 could affect the accuracy of the rheological data collected by drop-in unit 36.

The size and configuration of the openings of debris protector 52 would depend on the composition of the drilling fluid and will depend on the smallest dimension of the fluid flow path through drop-in unit 36 downstream of debris protector 52. The smallest dimension of the fluid flow path through drop-in unit 36 downstream of debris protector 52 may be, as an example, as a result of instrumentation located within the fluid flow path or a change in the inner diameter of a unit section 38. The size of the openings of debris protector 52 can be selected to prevent accumulation of debris at the smallest dimension of the fluid flow path through drop-in unit 36 downstream of debris protector 52. In an embodiment that includes an optional debris protector 52, the openings may be, as an example, twenty percent smaller than the smallest dimension of the fluid flow path through drop-in unit 36 downstream of debris protector 52.

After passing through opening 50, drilling fluid will travel through the series of unit sections 38 that are downstream of entry funnel 40. The series of unit sections 38B-38E are each elongated tubular members with an inner bore. When jointed together, the series of unit sections 38B-38E define instrumentation tubular 54. Instrumentation tubular 54 is an elongated member with an inner bore that is in fluid communication with opening 50 through the end plate 48. As further described, instrumentation tubular 54 can be made up of a series of unit sections, each of which can have an unimpeded inner bore, can have no sensors, can have a sensor, can have a reduction in internal diameter, or can have a combination of any such features.

In the example embodiments of FIGS. 2-3, unit section 38B which is adjacent to entry funnel 40 is shown as a tubular member without any sensors. Unit section 38B can be an elongated member with an unimpeded inner bore. The number of such sensorless tubular members can vary between job sites. As an example, the number of sensorless unit sections can be selected so that a laminar flow, or a nearly laminar flow is established within the series of units sections 38 upstream of a unit section that includes a sensor for flow measurement.

Unit section 38C is downstream of and adjacent to unit section 38B. Unit section 38D is in turn downstream of and adjacent to unit section 38B. In addition, unit section 38E is in turn downstream of and adjacent to unit section 38C. Each of the unit sections 38C-38E include a sensor 56. Sensor 56 can be a low power sensor that can be battery operated or can be solar power operated so that no power cables external to stand alone drop-in unit 36 are required to power sensor 56 during operation of drop-in unit 36 within mud line 32.

Sensor 56 can be, for example, a pressure sensor, temperature sensor, or flow rate sensor. In embodiments of this disclosure, instrumentation tubular 54 includes downstream sensor 58 and upstream sensor 60. Downstream sensor 58 is positioned within instrumentation tubular 54 downstream of upstream sensor 60. Downstream sensor 58 and upstream sensor 60 can sense a parameter of the drilling fluid that is traveling through the inner bore of instrumentation tubular 54. The data collected by downstream sensor 58 and upstream sensor 60 can be used for calculating a change of viscosity of the drilling fluid within mud line 32 over time.

In example embodiments, downstream sensor 58 includes a downstream pressure sensor and upstream sensor 60 includes an upstream pressure sensor. The pressure sensors can sense a pressure of the drilling fluid that is traveling through the inner bore of instrumentation tubular 54 of drop-in unit 36. The change in pressure between pressure sensors can be calculated and used to determine a change in viscosity of the drilling fluid traveling through mud line 32 over time.

Downstream sensor 58 can further include a downstream temperature sensor and upstream sensor 60 can further include an upstream temperature sensor. The temperature sensor can be combined with the pressure sensor or can be a separate sensor. The temperature sensors can sense a temperature of the drilling fluid that is traveling through drop-in unit 36. The sensed temperatures can be used for calculating a temperature corrected change of viscosity of the drilling fluid within mud line 32 over time.

Sensors 56 can further include flow rate sensor 62. Flow rate sensor 62 can be used to measure a flow rate of the drilling fluid within drop-in unit 36. In an embodiment, flow rate sensor 62 can be positioned downstream of any other of the sensors so that any turbulence or drop in pressure caused by flow rate sensor 62 does not affect measurements obtained by such other sensors. The flow rate can further be used to calculate a flow rate dependent change in viscosity of the drilling fluid within mud line 32 over time.

Measurements and data obtained by sensors 56 can be communicated wirelessly to a remote site. In such embodiments, the measurements and data can be communicated by, for example, a wi-fi signal, a 4G LTE signal, or other known form of wireless telemetry. The measurements and data obtained by sensors 56 can be transmitted through transmitter 64, which can extend radially outward of mud line 32. Alternately, transmitter 64 can be a cable that is wired to local computer that is used to gather measurements and data obtained by sensors 56.

Figure 10:
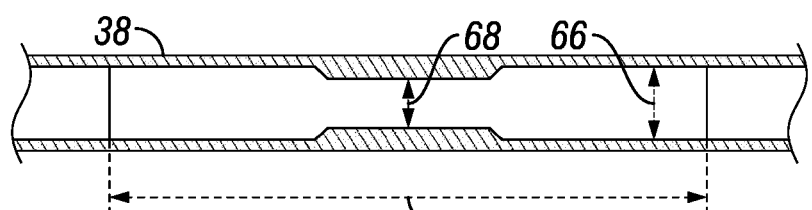
FIG. 10 is a detailed section view of a unit section of the drop-in unit, in accordance with an embodiment of this disclosure.

Looking at FIG. 10, unit section 38 can alternately include a change in diameter of the inner bore. The unit section 38 that includes a change in diameter can have a larger inner diameter 66 located at end sections of the inner bore of unit section 38. Such unit section 38 will include a portion with a smaller inner diameter 68. A pressure sensor can be located upstream of the reduced diameter, along the reduced diameter, and downstream of the reduced diameter. The reduction in diameter of the inner bore will result in different pressure readings by such pressure sensors, which can be used for calculating a viscosity. In embodiments of this disclosure, the smaller inner diameter 68 will have a minimum diameter of at least 76 millimeters. A diameter smaller than 76 millimeters could be prone to blockage by components of the drilling fluid.

Looking at FIGS. 2-3, anchor section 42 can secure drop-in unit 36 within mud line 32. Anchor section 42 is secured to an upstream unit section 38 of drop-in unit 36 so that when anchor section 42 is statically connected to mud line 32, secure drop-in unit 36 will remain static within mud line 32. In the example embodiment of FIG. 2, anchor section 42 includes a flange connector. The flange connector is a vertically oriented plate that can be sandwiched between end faces of flange connectors of adjacent joints of mud line 32.

In the example embodiment of FIG. 3, anchor section 42 is instead anchored to an inner diameter of mud line 32. As an example, a hole could be drilled through a sidewall of mud line 32 and a fastener can be used to pass through the hole and engage drop-in unit 36.

Figure 11:
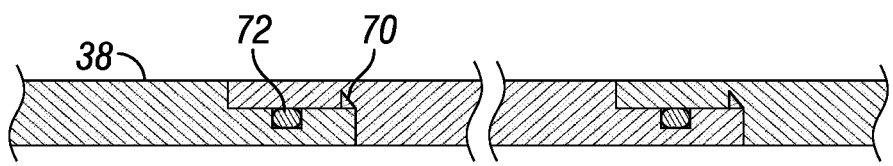
FIG. 11 is a section view of a sidewall of unit sections of the drop-in unit, secured to adjacent unit sections, in accordance with an embodiment of this disclosure.
Figure 12:
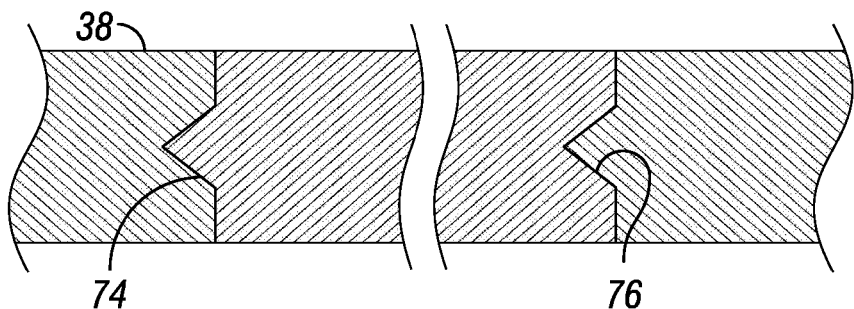
FIG. 12 is a top view of unit sections of the drop-in unit, secured to adjacent unit sections, in accordance with an embodiment of this disclosure, shown with an alignment apparatus.

Looking at FIG. 11, unit sections 38 can be sealingly secured to adjacent unit sections 38. In the example embodiment of FIG. 11, a portion of unit section 38 overlaps a portion of an adjacent unit section 38. Unit section 38 can be secured to an adjacent unit section 38 with a quick-connect connector. Adjacent unit sections 38 can be secured together with a press fit. As an alternate example, unit sections 38 can be secured to an adjacent unit section 38 by a protrusion 70. Protrusion 70 can click into a groove of the adjacent unit section 38. Alternately, the quick connect connector can include a snap ring, a spring held pin, a wire, a sprung ball, or other known reversible quick connect connector.

When each of the unit sections 38 are secured to adjacent unit sections 38, seal member 72 can seal between an outer diameter surface of one of the unit sections 38 and the inner diameter surface of an adjacent unit section 38. Seal member 72 prevents the flow of fluid past seal member 72 between adjacent unit sections 38.

In order to ensure the correct circumferential alignment between adjacent unit sections 38, an alignment apparatus can be part of unit section 38. In the example embodiment of claim 12, the alignment apparatus includes an extended member 74 in a sidewall of a unit section 38, and a corresponding notch 76 in a sidewall of an adjacent unit section 38. Extended member 74 and notch 76 have matching shapes so that extended member 74 fits within notch 76. In this way, there is only one circumferential orientation in which adjacent unit sections 38 can be sealingly secured to each other. When connecting a unit section 38 to an adjacent unit section 38, one or both of the unit sections 38 can be rotated relative to the other around a central axis of the unit section until extended member 74 is aligned with notch 76. Then unit sections 38 can be releasably secured together with a quick connect connection.

In an example of operation, in order to monitor rheological characteristics of drilling fluid flowing through a drilling fluid circulation system, drop-in unit 36 is installed within a flow line, such as in mud line 32. Drop-in unit 36 can be used to recognize changes in the rheological characteristics of the drilling fluid over time. At a first time, a first downstream fluid parameter of the drilling fluid traveling through the inner bore of instrumentation tubular 54 can be measured at the downstream sensor, and a first upstream parameter of the drilling fluid traveling through the inner bore of instrumentation tubular 54 can be measured at the upstream sensor. These measured values can be used to calculate a first fluid viscosity. As an example, the difference in pressure over the distance between the upstream sensor and the downstream sensor can be used to calculate the viscosity of the drilling fluid at the first time.

Temperatures can also be measured at the upstream and downstream sensors at the first time to further define the first fluid viscosity that is corrected for temperature. The flow rate of the drilling fluid traveling through instrumentation tubular 54 can be measured at a first time to define the second fluid viscosity at such flow rate at the first time.

At a second time, a second downstream fluid parameter of the drilling fluid traveling through the inner bore of instrumentation tubular 54 can be measured at the downstream sensor, and a second upstream parameter of the drilling fluid traveling through the inner bore of instrumentation tubular 54 can be measured at the upstream sensor. These measured values can be used to calculate a second fluid viscosity. As an example, the difference in pressure over the distance between the upstream sensor and the downstream sensor can be used to calculate the viscosity of the drilling fluid.

Temperatures can also be measured at the upstream and downstream sensors at the second time to further define the second fluid viscosity that is corrected for temperature. The flow rate of the drilling fluid traveling through instrumentation tubular 54 can be measured at a second time to define the second fluid viscosity at such flow rate at the second time.

The second fluid viscosity can be compared to the first fluid viscosity to determine a change of viscosity of the drilling fluid within the flowline between the first time and the second time. These changes can be monitored in real-time to provide an indication of viscosity change the drilling fluid during the drilling operations.

In certain embodiments, the viscosity readings can further be combined with standard lab results taken at various flow rates using a predictive trend analysis software package. Predictive algorithms can use the detailed measurements from the lab results that are taken using standard API recommended equipment and conditions at given time intervals, together with the trend analysis obtained from the drop-in unit to predict drilling fluid properties in real time from the mud return line.

Embodiments described in this disclosure therefore provide a drop-in unit that can provide autonomous, continuous monitoring of drilling fluid viscosity change. In systems and methods of this disclosure the flow rate through the drop-in unit is not controlled. Control of the flow rate would be necessary to obtain viscosity readings over numerous selected and known flow rates if accurate absolute viscosity information was required. The data collected by the drop-in unit can instead be used for indicative trend analysis and for monitoring of changing properties of the frilling fluid. The drop-in unit is self-contained and installation of the drop-in unit does not require modification to the current drilling fluid circulation system. The drop-in unit is positioned within the drilling fluid circulation system upstream of mud shakers. Measurements of the properties of the drilling fluid with cuttings may lead to data analysis of drilling fluid cuttings volume also in real time.

Embodiments of this disclosure, therefore, are well adapted to carry out the objects and attain the ends and advantages mentioned, as well as others that are inherent. While embodiments of the disclosure has been given for purposes of disclosure, numerous changes exist in the details of procedures for accomplishing the desired results. These and other similar modifications will readily suggest themselves to those skilled in the art, and are intended to be encompassed within the spirit of the present disclosure and the scope of the appended claims.

What is claimed is:

1. A system for determining rheology characteristics of a drilling fluid, the system including:
   a drop-in unit sized to fit within a flowline of a drilling fluid circulation system upstream of a mud shaker, the drop-in unit having:
   an entry funnel, the entry funnel having an entrance end oriented with an entrance facing in an upstream direction within the flowline, and a tube end opposite the entrance end, the tube end having an end plate with an opening through the end plate, the entrance end having an outer diameter that is larger than a diameter of the opening through the end plate; and
   an instrumentation tubular, the instrumentation tubular being an elongated member with an inner bore that is in fluid communication with the opening through the end plate, where the instrumentation tubular includes a downstream sensor and an upstream sensor; where the upstream sensor and the downstream sensor are operable to sense a parameter of the drilling fluid traveling through the inner bore of the instrumentation tubular for calculating a change of viscosity of the drilling fluid within the flowline between a first time and a second time.

2. The system of claim 1, further including an anchor section at a downstream end of the drop-in unit operable to anchor the drop-in unit within the flowline.

3. The system of claim 1, further including a flange connector located at a downstream end of the drop-in unit, operable to connect the drop-in unit to a flange of the flowline.

4. The system of claim 1, where the end plate has a vertical height such that the end plate acts as a weir, increasing a height of a level of fluid upstream of the end plate compared to a height of a level of fluid downstream of the end plate.

5. The system of claim 1, further including a debris protector extending across the entrance end of the entry funnel, the debris protector having openings sized to allow a passage of fluid through the debris protector and to prohibit a passage of certain debris through the debris protector.

6. The system of claim 1, where the inner bore of the instrumentation tubular includes a change in diameter between the downstream sensor and the upstream sensor.

7. The system of claim 1, where the downstream sensor includes a downstream pressure sensor and the upstream sensor includes an upstream pressure sensor.

8. The system of claim 7, where the downstream sensor further includes a downstream temperature sensor and the upstream sensor further includes an upstream temperature sensor, the downstream temperature sensor and the upstream temperature sensor operable to sense a temperature of the drilling fluid traveling through the inner bore of the instrumentation tubular, for calculating a temperature corrected change of viscosity of the drilling fluid within the flowline between the first time and the second time.

9. The system of claim 1, where the drop-in unit is formed of a plurality of unit sections, each of the unit sections secured to an adjacent unit section with a quick-connect connector.

10. The system of claim 9, further including an alignment apparatus operable to circumferentially orient each of the unit sections to the adjacent unit section.

11. The system of claim 9, where each of the unit sections has a length in a range of 1 meter to 1.5 meters and has a diameter in a range of 76 millimeters to 152 millimeters.

12. A method for determining rheology characteristics of a drilling fluid, the method including:

installing a drop-in unit within a flowline of a drilling fluid circulation system upstream of a mud shaker, the drop-in unit having:

an entry funnel, the entry funnel having an entrance end oriented with an entrance facing in an upstream direction within the flowline, and a tube end opposite the entrance end, the tube end having an end plate with an opening through the end plate, the entrance end having an outer diameter that is larger than a diameter of the opening through the end plate; and an instrumentation tubular, the instrumentation tubular being an elongated member with an inner bore that is in fluid communication with the opening through the end plate, where the instrumentation tubular includes a downstream sensor and an upstream sensor;

at a first time, sensing a first downstream fluid parameter of the drilling fluid traveling through the inner bore of the instrumentation tubular at the downstream sensor, and sensing a first upstream parameter of the drilling fluid traveling through the inner bore of the instrumentation tubular at the upstream sensor, and calculating a first fluid viscosity;

at a second time, sensing a second downstream fluid parameter of the drilling fluid traveling through the inner bore of the instrumentation tubular at the downstream sensor, and sensing a second upstream parameter of the drilling fluid traveling through the inner bore of the instrumentation tubular at the upstream sensor, and calculating a second fluid viscosity; and comparing the second fluid viscosity to the first fluid viscosity to determine a change of viscosity of the drilling fluid within the flowline between the first time and the second time.

13. The method of claim 12, further including anchoring a downstream end of the drop-in unit within the flowline.

14. The method of claim 12, further including securing a downstream end of the drop-in unit to a flange of the flowline.

15. The method of claim 12, where the inner bore of the instrumentation tubular includes a change in diameter between the downstream sensor and the upstream sensor.

16. The method of claim 12, further including increasing a height of a level of fluid upstream of the end plate compared to a height of a level of fluid downstream of the end plate by providing the end plate with a vertical height such that the end plate acts as a weir.

17. The method of claim 12, further including a debris protector extending across the entrance end of the entry funnel, the debris protector having openings sized to allow a passage of fluid through the debris protector and to prohibit a passage of certain debris through the debris protector.

18. The method of claim 12, where the downstream sensor includes a downstream pressure sensor and the upstream sensor includes an upstream pressure sensor.

19. The method of claim 18, where the downstream sensor further includes a downstream temperature sensor and the upstream sensor further includes an upstream temperature sensor, the method further including:

at the first time, measuring a first downstream temperature and a first upstream temperature of the drilling fluid traveling through the inner bore of the instrumentation tubular, and calculating a temperature corrected first fluid viscosity;

at the second time, measuring a second downstream temperature and a second upstream temperature of the drilling fluid traveling through the inner bore of the instrumentation tubular, and calculating a temperature corrected second fluid viscosity; and determining a temperature corrected change of viscosity of the drilling fluid within the flowline between the first time and the second time.

20. The method of claim 12, further including forming the drop-in unit from a plurality of unit sections, each of the unit sections secured to an adjacent unit section with a quick-connect connector.

21. The method of claim 20, further including circumferentially orienting each of the unit sections to the adjacent unit section with an alignment apparatus.

22. The method of claim 20, where each of the unit sections has a length in a range of 1 meter to 1.5 meters and has a diameter in a range of 76 millimeters to 152 millimeters.

\* \* \* \* \*